(12) United States Patent
Chung et al.

(10) Patent No.: US 10,815,214 B2
(45) Date of Patent: *Oct. 27, 2020

(54) REGIOSELECTIVE N-2 ARYLATION OF INDAZOLES

(71) Applicant: Merck Sharp & Dohme Corp., North Wales, PA (US)

(72) Inventors: Cheol K. Chung, Kenilworth, NJ (US); Mark E. Scott, Edmonton (CA); Paul G. Bulger, Jersey City, NJ (US); Kevin M. Belyk, Metuchen, NJ (US); John Limanto, Jersey City, NJ (US); Guy R. Humphrey, Hillsborough, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/576,133

(22) Filed: Sep. 19, 2019

(65) Prior Publication Data
US 2020/0010449 A1    Jan. 9, 2020

Related U.S. Application Data

(63) Continuation of application No. 15/419,618, filed on Jan. 30, 2017, now Pat. No. 10,435,386, which is a continuation of application No. 14/649,299, filed as application No. PCT/US2013/072710 on Dec. 3, 2013, now Pat. No. 9,580,407.

(60) Provisional application No. 61/734,392, filed on Dec. 7, 2012.

(51) Int. Cl.
*C07D 401/10*    (2006.01)

(52) U.S. Cl.
CPC .................................. *C07D 401/10* (2013.01)

(58) Field of Classification Search
CPC .................................................. C07D 401/10
See application file for complete search history.

(56) References Cited

U.S. PATENT DOCUMENTS

| 7,199,147 | B2 | 4/2007 | Imazaki et al. |
| 8,071,623 | B2 | 12/2011 | Jones et al. |
| 8,129,377 | B2 | 3/2012 | Watanabe et al. |
| 2010/0286203 | A1 | 11/2010 | Foley et al. |

FOREIGN PATENT DOCUMENTS

| WO | 2007113596 A1 | 10/2007 | |
| WO | WO-2008027466 A1 * | 3/2008 | |
| WO | 2008084261 A1 | 7/2008 | |
| WO | 2012074126 A1 | 6/2012 | |
| WO | 2012107850 A1 | 8/2012 | |
| WO | WO-2012168260 A1 * | 12/2012 | ........... C07D 413/12 |

OTHER PUBLICATIONS

Pontiki "Quantitative structure activity relationships (QSAR) of substituted (S)-phenylpiperidines as preferential dopamine autoreceptor antagonists." Journal of Enzyme Inhibition and Medicinal Chemistry, 2005, 20(1), 5-12.*
Bhat, Ramakrishna G "A mild and selective method for N-dealkylation of tertiary amines" Tetrahedron Letters, 2004, 45(43), 7983-7985.*
Olaffson, "A New Reagent for the Selective, High-Yield N-Dealkylation of Tertiary Amines: Improved Syntheses of Naltrexone and Nalbuphine" J. Org. Chem., 1984, vol. 49, No. 11, p. 2081-2082.*
Chemical Abstract Service Database CAPLUS 2012:1823601 Document No. 158:77257 for WO 2012168260 A1 Dec. 13, 2012.*
Colpaert "Asymmetric Synthesis of Chiral N-Sulfinyl 3-Alkyl- and 3-Arylpiperidines by .alpha.-Alkylation of N-Sulfinyl Imidates with 1-Chloro-3-iodopropane." Journal of Organic Chemistry, 2011, 76(1), 234-244, Published on Web Dec. 1, 2010.*
Antilla et al., "Copper-Diamine-Catalyzed N-Arylation of Pyrroles, Pyrazoles, Indazoles, Imidazoles and Triazoles," J. Org. Chem (2004); 69:5578-5587.
Chung et al., "Process Development of C—N Cross-Coupling and Enantioselective Biocatalytic Reactions for the Asymmetric Synthesis of Niraparib," Organic Process Research & Development (2014); 18(1):215-227.
Jones et al., "Discovery of 2-[4-[(3S)-Piperidin-3-yl]-2H-indazole-7-carboxamide (MK-4827): A Novel Oral Poly(ADP-ribose) polymerase (PARP) Inhibitor Efficacious in BRCA-1 and -2 Mutant Tumors," Journal of Medicinal Chemistry (2009); 52(22):7170-7185.

(Continued)

Primary Examiner — David K O'Dell
(74) Attorney, Agent, or Firm — Fox Rothschild LLP

(57) ABSTRACT

A novel process is provided for the efficient preparation of an asymmetric compound of structural formula I:

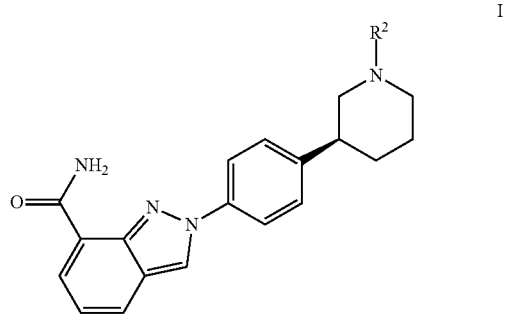

comprising a copper-catalyzed, carbon-nitrogen cross-coupling step. The process described as part of the present invention can be used to manufacture poly (ADP-ribose) polymerase (PARP) inhibitors, which may be useful for the treatment of cancer. In particular, the present invention describes a process for the manufacture of the PARP inhibitor, 2-{4-[(3S)-piperidin-3-yl]phenyl}-2H-indazole-7-carboxamide.

8 Claims, No Drawings
Specification includes a Sequence Listing.

(56) References Cited

OTHER PUBLICATIONS

Online: "http://web/archive.org/web/20070202005900/http://www.ambinter.com/" dated Feb. 2, 2007, accessed Feb. 28, 2013.
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, acessed Apr. 1, 2015.
STN—Chemical Database Registry entry RN 1209934-80-4 for N-(1-phenylethyl)-1H-indazole-7-carboxamide, Entered STN: Mar. 15, 2010.
STN—Chemical Database Registry entry RN 1088181-79-6 for N-(4-methoxyphenyl)-1H-indazole-7-carboxamide, Entered STN: Dec. 22, 2008.
STN—Chemical Database Registry entry RN 1147378-81-1 for N-(1,1-dimethylpropyl)-1H-indazole-7-carboxamide, Entered STN: May 19, 2009.
STN—Chemical Database Registry entry RN 1088176-59-3 for N-butyl-1H-indazole-7-carboxamide, Entered STN: Dec. 22, 2008.
Wallace et al., "Development of a Fit-for-Purpose Large-Scale Synthesis of an Oral PARP Inhibitor," Organic Process Research & Development (2011); 15(4):831-840.

\* cited by examiner

REGIOSELECTIVE N-2 ARYLATION OF INDAZOLES

CROSS-REFERENCE TO RELATED APPLICATIONS

The present application is a continuation of U.S. application Ser. No. 15/419,618, filed on Jan. 30, 2017, which is a continuation of U.S. application Ser. No. 14/649,299, filed on Jun. 3, 2015, now U.S. Pat. No. 9,580,407, which is a U.S. National Phase application under 35 U.S.A. § 371 of PCT Application No. PCT/US2013/072710, filed on Dec. 3, 2013, which in turn claims the benefit of U.S. Provisional Application No. 61/734,392, filed on Dec. 7, 2012, all of which are hereby incorporated by reference in their entireties.

REFERENCE TO SEQUENCE LISTING

A sequence listing text file is submitted via EFS-Web in compliance with 37 CFR § 1.52(e)(5) concurrently with the specification. The sequence listing has the file name "23369-PCT-SEQTXT-15 Oct. 2013", was created on Oct. 15, 2013, and is 6,297 bytes in size. The sequence listing is part of the specification and is incorporated in its entirety by reference herein.

BACKGROUND OF THE INVENTION

This invention describes the synthesis of the poly (ADP-ribose) polymerase (PARP) inhibitor, 2-{4-[(3S)-Piperidin-3-yl]phenyl}-2H-indazole-7-carboxamide, comprising an optimized copper-catalyzed carbon-nitrogen coupling process utilizing a protecting group strategy. A crucial step in the synthesis of 2-{4-[(3S)-Piperidin-3-yl]phenyl}-2H-indazole-7-carboxamide includes coupling of a key piperidine intermediate with N-2 of a key indazole intermediate. Protecting a primary amide of the parent indazole used in the cross-coupling reaction results in a more efficient process with improved reactivity and regioselective N-2 arylation.

Buchwald et al. (U.S. Pat. No. 6,235,936) describes methods for the metal-catalyzed arylation of hydrazines, hydrazones, hydroxylamines and/or oximes through the formation of a carbon-heteroatom bond between an aromatic compound comprising an activated carbon bearing a leaving group and a heteroatom of a hydrazine, hydrazone, hydroxylamine or oxime.

PCT International Appl. No. PCT/US02/12785 (published WO 2002085838) describes copper-catalyzed methods for forming carbon-carbon and carbon-heteroatom bonds.

U.S. Pat. No. 8,071,623 describes PARP inhibitors, including 2-{4-[(3S)-Piperidin-3-yl]phenyl}-2H-indazole-7-carboxamide and a synthesis of this compound.

Wallace et al. (2011, Organic Process Research and Development 15:831-840) describes large-scale synthesis (up to 5 kg) routes of 2-{4-[(3S)-Piperidin-3-yl]phenyl}-2H-indazole-7-carboxamide relying on either classical resolution or chiral separation.

SUMMARY OF THE INVENTION

The present invention relates to a method for the preparation of a compound of formula I:

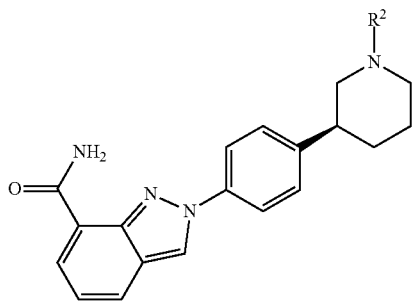

wherein $R^2$ is hydrogen or an amine protecting group, comprising copper-catalyzed carbon-nitrogen cross-coupling of a piperidine compound and an indazole intermediate. The process described as part of the present invention can be used to manufacture poly (ADP-ribose) polymerase (PARP) inhibitors disclosed in U.S. Pat. No. 8,071,623, which may be useful for the treatment of cancer. In particular, the present invention describes a process for the manufacture of the PARP inhibitor, 2-{4-[(3S)-Piperidin-3-yl]phenyl}-2H-indazole-7-carboxamide.

DETAILED DESCRIPTION OF THE INVENTION

The present invention provides an efficient process for the preparation a compound of formula I:

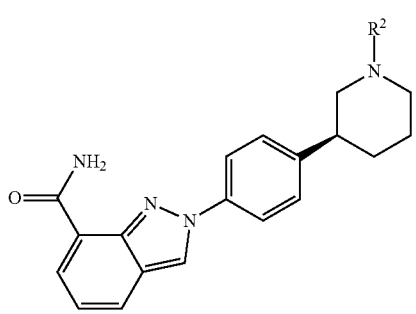

wherein $R^2$ is hydrogen or an amine protecting group, comprising:

(a) carbon-nitrogen cross-coupling of (i) an indazole of formula II containing a protected amide:

wherein $R^1$ is $C_{1-8}$ alkyl, $C_{3-8}$ cycloalkyl, $C_{4-8}$ heterocyclyl, aryl, heteroaryl or aryl$C_{1-8}$alkyl, optionally substituted with one to three aryl, heteroaryl, $C_{3-8}$ cycloalkyl or $OC_{1-8}$ alkyl; and (ii) a piperidine compound of formula III:

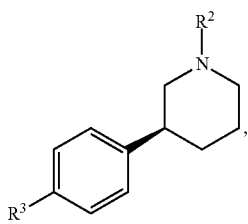

wherein R³ is a leaving group and R² is as provided above, in the presence of a catalytic amount of a copper salt, a suitable ligand, a base, and a solvent, forming a compound of formula IV:

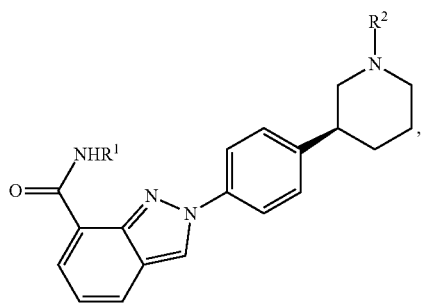

wherein R¹ and R² are as provided above; and,
(b) de-protecting the amide of the compound of formula IV.

In one embodiment of the process of the present invention, the copper salt is a Cu(I) or Cu(II) salt. Examples of copper salts that can be used in the disclosed process CuI, CuCl, CuCl₂, CuBr, CuBr.S(CH₃)₂, CuBr₂, CuF₂, CuOAc, Cu(OAc)₂, Cu₂O, CuO, CuSO₄, Cu(OTf)₂, Cu(OMs)₂, Cu(OTs)₂, Cu(NO₃)₂, Cu(BF₄)₂CuBr and (nBu₄-N)₂(CuI₂)₂ (Maligres, P. E. et al., 2012, *J. Org. Chem.* 77:7646-7651). In a further embodiment, the copper salt is CuBr. In another embodiment, the copper salt is CuI.

The copper salt used in the process of the present invention is present in an amount suitable to achieve efficient catalysis. The copper salt is typically present in an amount of 1-20 mol %. In one embodiment, the copper salt is present in an amount less than or equal to about 10 mol % relative to the piperidine compound (e.g., a compound of formula III or the compound of formula VIII, infra). In another embodiment, the copper salt is present in an amount less than or equal to about 5 mol % relative to the piperidine compound. In a further embodiment, the copper salt is present in an amount less than or equal to about 1 mol % relative to the piperidine compound. In one embodiment, the copper salt used in the present invention is CuBr and is present in an amount less than or equal to about 5 mol % relative to the piperidine compound. In another embodiment, the copper salt is CuBr and is present in an amount of about 5 mol % relative to the piperidine compound. In another embodiment, the copper salt used in the present invention is CuI and is present in an amount less than or equal to about 10 mol % relative to the piperidine compound. In a further embodiment, the copper salt is CuI and is present in an amount of about 7.5 mol % relative to the piperidine.

In one embodiment, R¹ is $C_{1-8}$ alkyl, $C_{3-8}$ cycloalkyl, $C_{4-8}$ heterocyclyl, aryl, heteroaryl or aryl$C_{1-3}$alkyl, optionally substituted with one to three phenyl ("Ph"), $C_3$ cycloalkyl or methoxy. In a further embodiment, R¹ is:

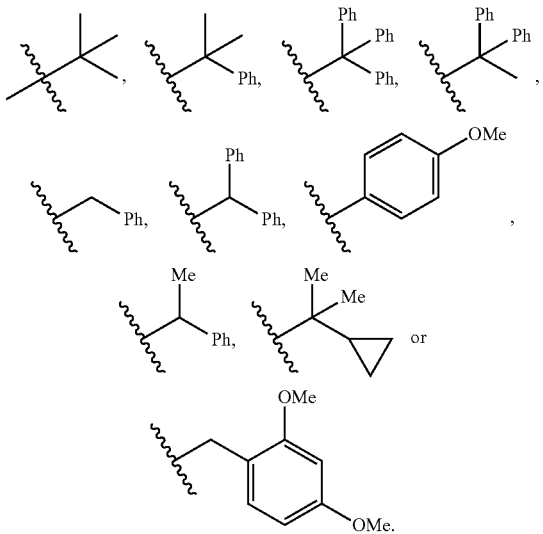

In a further embodiment, R¹ is:

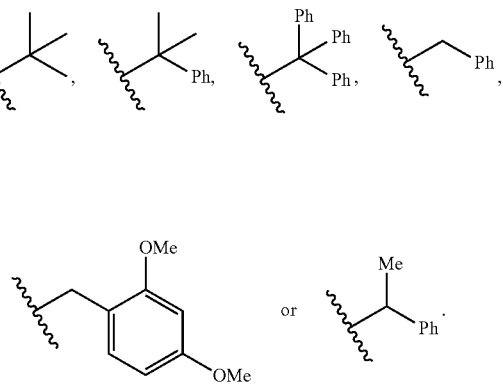

In another embodiment, R¹ is tert-butyl, cumyl (—C(CH₃)₂Ph) or trityl (—C(Ph)₃). In a still further embodiment, R¹ is tert-butyl.

In one embodiment of the invention, R² is an amine protecting group. Examples of amine protecting groups that can be used are formyl, acetyl, trifluoroacetyl, benzyl, benzoyl, carbamate, benzyloxycarbonyl, p-methoxybenzyl carbonyl, tert-butoxycarbonyl, trimethylsilyl, 2-trimethylsilyl-ethanesulfonyl, trityl and substituted trityl groups, allyloxycarbonyl, 9-fluorenylmethyloxycarbonyl, nitro-veratryloxycarbonyl, p-methoxybenzyl and tosyl. In a further embodiment, R² is the amine protecting group tert-butoxycarbonyl ("Boc").

In one embodiment, R³ is Br or I. In a further embodiment, R³ is Br.

If R² is an amine protecting group, including but not limited to tert-butoxycarbonyl ("Boc"), the process of the present invention may further comprise a step wherein the piperidyl nitrogen of the compound of formula IV is deprotected, forming the compound of formula V:

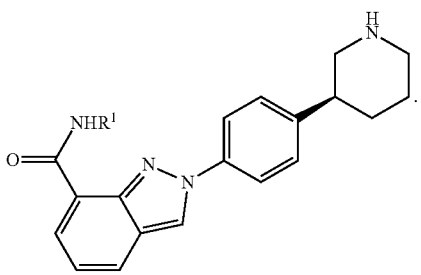

V

De-protection of the piperidyl nitrogen of the compound of formula IV may occur at the same time (i.e., during the same reaction) as the de-protection of the amide of that compound.

Thus, in one embodiment, the present invention provides an efficient process for the preparation a compound of formula V:

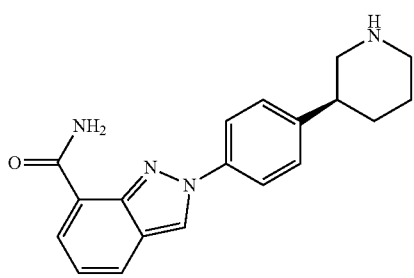

V comprising:

(a) carbon-nitrogen cross-coupling of (i) an indazole of formula II containing a protected amide:

II wherein $R^1$ is $C_{1-8}$ alkyl, $C_{3-10}$ cycloalkyl, $C_{4-10}$ heterocyclyl, aryl, or heteroaryl, and wherein said alkyl group is optionally substituted with one to three aryl or heteroaryl; and (ii) a piperidine compound of formula III:

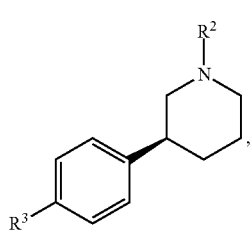

III wherein $R^3$ is a leaving group and $R^2$ is an amine protecting group; in the presence of a catalytic amount of a copper salt, a suitable ligand, a base, and a solvent, forming a compound of formula IV:

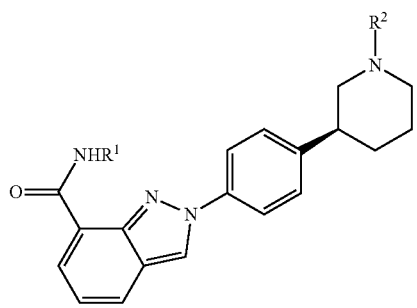

IV wherein $R^1$ and $R^2$ are as provided above; and, (b) de-protecting both the amide and the piperidyl nitrogen of the compound of formula IV, forming the compound of formula V.

The de-protecting step of part (b) can occur in a one-step or two-step process. For example, in one embodiment, deprotection of the amide and deprotection of the piperidyl nitrogen occur in single reaction (i.e., one-step process). In another embodiment, the amide is de-protected first (in one reaction), followed by de-protection of the piperidyl nitrogen (in a separate reaction). In a further embodiment, the piperidyl nitrogen is de-protected first, followed by deprotection not the amide.

In another embodiment of a process of the invention, $R^1$ is tert-butyl, $R^2$ is tert-butoxycarbonyl, and $R^3$ is Br.

The present invention further relates to a process for preparing a compound of formula VI:

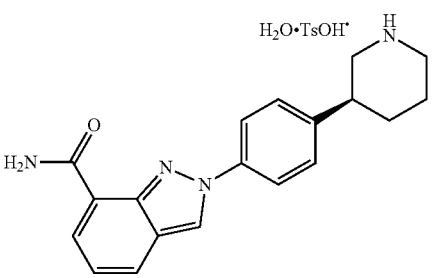

VI comprising:

(a) carbon-nitrogen cross-coupling of (i) the indazole of formula VII and (ii) the piperidine compound of formula VIII, wherein Boc is tert-butoxycarbonyl:

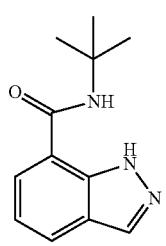

VII

VIII

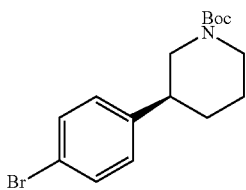

in the presence of a catalytic amount of a copper salt, a suitable ligand, a base, and a solvent, forming the compound of formula IX:

IX

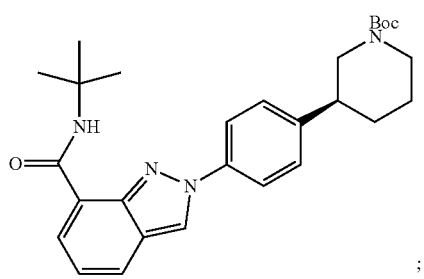

and, (c) de-protecting both the amide and the piperidyl nitrogen of the compound of formula IX in the presence of p-TsOH (aq), forming the compound of formula VI.

The de-protecting step of part (c) can occur in a one-step or two-step process. For example, in one embodiment, deprotection of the amide and deprotection of the piperidyl nitrogen occur in single reaction (i.e., one-step process). In another embodiment, the amide is de-protected first (in one reaction), followed by de-protection of the piperidyl nitrogen (in a separate reaction). In a further embodiment, the piperidyl nitrogen is de-protected first, followed by deprotection nof the amide.

In an embodiment of a process of the invention, the ligand present in the carbon-nitrogen coupling reaction is selected from dimethylglycine, 8-hydroxyquinoline, phenanthroline, neocuproine, 3,4,7,8-tetramethyl-1,10-phenanthroline, 2,2,6,6-tetramethyl-3,5-heptanedione, 2,6-dimethyl-3,5-heptanedione, 2-isobutyrylcyclohexanone, 2-acetylcyclohexanone, 2,4-pentanedione, 3,5-heptanedione, and N,N'-dimethylcyclohexane-1,2-diamine. In a further embodiment, the ligand is selected from dimethylglycine, 8-hydroxyquinoline and N,N'-dimethylcyclohexane-1,2-diamine. In a still further embodiment, the ligand is 8-hydroxyquinoline. In another embodiment, the ligand is N,N'-dimethylcyclohexane-1,2-diamine. In one embodiment, the ligand is present in an amount less than or equal to about 40 mol % relative to the piperidine intermediate (i.e., a compound of formula III of the compound of formula VIII). In a further embodiment, the ligand is present in an amount less than or equal to about 30 mol % relative to the piperidine intermediate. In another embodiment, the ligand is present in an amount less than or equal to about 20 mol % relative to the piperidine intermediate. In a still further embodiment, the ligand is present in an amount less than or equal to about 10 mol % relative to the piperidine intermediate.

In a further embodiment of the invention, the base present in the carbon-nitrogen coupling step is a carbonate, phosphate, oxide, hydroxide, alkoxide, aryloxide, amine, metal amide, fluoride, or guanidine. In certain embodiments, the base is selected from $K_2CO_3$, $K_3PO_4$, $K_2HPO_4$, $Cs_2CO_3$, $KHCO_3$, $Na_2CO_3$ or $NaHCO_3$, or mixtures thereof. In another embodiment, the base is $K_2CO_3$. In a further embodiment, the base is $K_3PO_4$. Typically, there is no need to use large excesses of base in the process of the present invention. In certain embodiments, no more than four equivalents of base are used, relative to the piperidine reactant. In other embodiments, no more than two equivalents of base are used, relative to the piperidine reactant In one embodiment, the solvent present in the carbon-nitrogen coupling reaction is selected from dimethyl sulfoxide (DMSO), dimethylformamide (DMF), dimethylacetamide (DMAc), 1,3-dimethyl-2-imidazolidinone (DMI), N-methyl-2-pyrrolidone (NMP), sulfolane, pyridine, 2-picoline, 3-picoline, 4-picoline, toluene, o-xylene, m-xylene, p-xylene, dioxane, chlorobenzene, anisole and any combinations thereof. In a further embodiment, the solvent is selected from dimethyl sulfoxide (DMSO), dimethylacetamide (DMAc) and toluene. In a still further embodiment, the solvent is dimethylacetamide (DMAc). In another embodiment, the solvent is toluene. In one embodiment, the solvent is present in the carbon-nitrogen coupling reaction within a range of between about 0.09 and about 1.4M.

The carbon-nitrogen coupling reaction may be performed at a temperature of between about 90° C. and 130° C. In one embodiment, the carbon-nitrogen coupling reaction is performed at a temperature of about 100° C. In another embodiment, the reaction is performed at a temperature of about 110° C.

In one embodiment of a process of the invention, the carbon-nitrogen coupling reaction is performed in the presence of CuBr, the ligand 8-hydroxyquinoline, the base $K_2CO_3$, and the solvent dimethylacetamide (DMAc), at a temperature of about 110° C. In a further embodiment, CuBr is present in an amount of about 5 mol % relative to the piperidine intermediate (i.e., a compound of formula III or the compound of formula VIII). In another embodiment, 8-hydroxyquinoline is present in an amount of about 10 mol % relative to the piperidine intermediate (i.e., a compound of formula III or the compound of formula VIII).

An indazole of formula II, used in the carbon-nitrogen coupling reaction step of the disclosed process, may be formed by reacting indazole-7-carboxylic acid

with an amine in the presence of an organic reagent used to convert carboxylic acids into amides (e.g., 1,1'-carbonyldiimidazole (CDI), O-(7-azabenzotriazol-1-yl)-N,N,N',N'-tetramethyluronium hexafluorophosphate (HATU), etc.). The amine used in the reaction depends on the $R^1$ substituent group of the specific formula II indazole to be synthesized. For example, to make an indazole of formula VII, containing a tert-butyl group on the amide, tert-butylamine is used in the reaction. To make an indazole of formula II containing a cumyl group on the amide, cumylamine is used in the reaction. Likewise, to make an indazole of formula II containing a trityl group on the amide, tritylamine is used in the reaction.

Thus, a process of the present invention further comprises a step, prior to the carbon-nitrogen coupling step, wherein the indazole of formula II is first synthesized, wherein $R^1$ of the indazole of formula II is $R^1$ is $C_{1-8}$ alkyl, $C_{3-8}$ cycloalkyl, $C_{4-8}$ heterocyclyl, aryl, heteroaryl or aryl$C_{1-8}$alkyl, optionally substituted with one to three aryl, heteroaryl, $C_{3-8}$ cycloalkyl or $OC_{1-8}$ alkyl, by reacting indazole-7-carboxylic acid with an amine, including but not limited to tert-butylamine, cumylamine and tritylamine, and an organic chemical capable of converting a carboxylic acid into an amide. In one embodiment, the indazole of formula VIII is synthesized by reacting indazole-7-carboxylic acid with tert-butylamine in the presence of CDI. In another embodiment, an indazole of formula II, where $R^1$ is cumyl (—C(CH$_3$)$_2$Ph), is synthesized by reacting indazole-7-carboxylic acid with cumylamine in the presence of HATU. In a further embodiment, an indazole of formula II, where $R^1$ is trityl (—C(Ph)$_3$), is synthesized by reacting indazole-7-carboxylic acid with triphenylmethyl amine in the presence of HATU. In another embodiment, an indazole of formula II, where $R^1$ is a benzyl group, is synthesized by reacting indazole-7-carboxylic acid with benzyl amine in the presence of HATU. In a still further embodiment, an indazole of formula II, where $R^1$ is a 2,4-dimethyloxybenzyl group, is synthesized by reacting indazole-7-carboxylic acid with 2,4-dimethyoxybenzyl amine in the presence of HATU. In another embodiment, an indazole of formula II, where $R^1$ is an alpha-methyl benzyl group, is synthesized by reacting indazole-7-carboxylic acid with alpha-methylbenzyl amine in the presence of HATU The piperidine compounds used in the carbon-nitrogen coupling reaction step of the disclosed process (i.e., compounds of formula III and formula VIII) may be formed by employing dynamic kinetic resolution (DKR) involving an enzymatic enantioselective amination reaction catalyzed by a transaminase. Methods of preparing such piperidine compounds are specifically described in co-filed provisional application entitled "Biocatalytic Transamination Process," U.S. Provisional Appl No. 61/734,394, incorporated by reference herein. For example, the asymmetric piperidine compound of formula VIII can be prepared by a process comprising:

(a) biocatalytic transamination of a compound of formula X or a compound of formula XI:

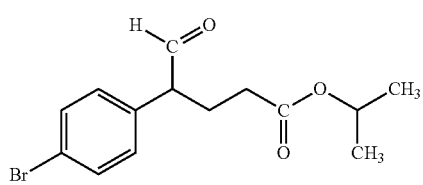

X

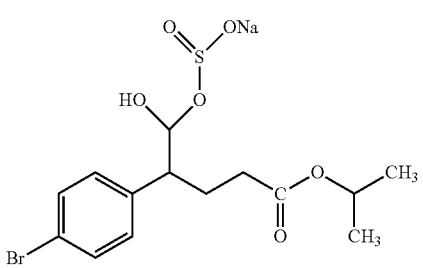

XI in the presence of a transaminase polypeptide, a coenzyme, and an amino donor, forming the compound of formula XII:

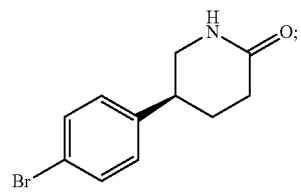

XII (b) reducing the lactam of the compound of Formula XII, forming the compound of Formula XIII:

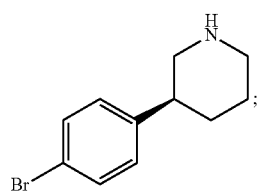

XIII and, (c) protecting the piperidine nitrogen of the compound of Formula XIII to form the compound of formula VIII.

Thus, a process of the present invention further comprises a step, prior to the carbon-nitrogen coupling step, wherein a piperidine compound of formula III or formula VIII is first synthesized by employing dynamic kinetic resolution (DKR) involving an enzymatic enantioselective amination reaction catalyzed by a transaminase. In one embodiment, the transaminase polypeptide is a naturally occurring transaminase. In another embodiment, the transaminase polypeptide is a synthetic variant of a naturally occurring transaminase. In a further embodiment, the transaminase polypeptide is selected from SEQ ID NO: 1 or SEQ ID NO: 2. In a further embodiment, the transaminase polypeptide is SEQ ID NO: 2. In another embodiment, isopropylamine is used as an amino donor. In a further embodiment, pyridoxal-phosphate is used as a coenzyme.

Definitions

For convenience, certain terms employed in the specification, examples, and appended claims are collected here.

"Amino donor" or "amine donor" refers to an amino compound which donates an amino group to an amino acceptor, thereby becoming a carbonyl species. Amino donors are molecules of general formula shown below,

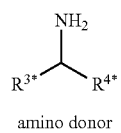

amino donor in which each of $R^{3*}$, $R^{4*}$, when taken independently, is an alkyl, an alkylaryl group, or aryl group which is unsubstituted or substituted with one or more enzymatically non-inhibiting groups. $R^{3*}$ can be the same or different from $R^{4*}$ in structure or chirality. $R^{3*}$ and $R^{4*}$, taken together, may form a ring that is unsubstituted, substituted, or fused to other rings. Typical amino donors include chiral and achiral amino acids, and chiral and achiral amines.

"Chiral amine" refers to amines of general formula $R^\alpha$—CH(NH$_2$)—$R^\beta$ and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^{\alpha}$ and $R^{\beta}$ above) also can vary widely and include alkyl, arylalkyl, aryl, halo, hydroxy, lower alkyl, lower alkyloxy, lower alkylthio, cycloalkyl, carboxy, carbalkyloxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, arylalkyl, or aryl substituted by the foregoing.

Exemplary amino donors include isopropylamine (also referred to as 2-aminopropane or "IPM"), α-phenethylamine (also termed 1-phenylethanamine) and its enantiomers (S)-1-phenylethanamine and (R)-1-phenylethanamine, 2-amino-4-phenylbutane, glycine, L-glutamic acid, L-glutamate, monosodium glutamate, L-alanine, D-alanine, D,L-alanine, L-aspartic acid, L-lysine, D,L-ornithine, β-alanine, taurine, n-octylamine, cyclohexylamine, 1,4-butanediamine (also referred to as putrescine), 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines.

"Amino acceptor" and "amine acceptor," "keto substrate," "keto," and "ketone" are used interchangeably herein to refer to a carbonyl (keto, or ketone) compound which accepts an amino group from a donor amine. Amino acceptors are molecules of general formula shown below,

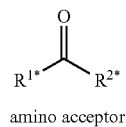

amino acceptor in which each of $R^{1*}$, $R^{2*}$, when taken independently, is an alkyl, an alkylaryl group, or aryl group which is unsubstituted or substituted with one or more enzymatically acceptable groups. $R^{1*}$ may be the same or different from $R^{2*}$ in structure or chirality. In some embodiments, $R^{1*}$ and $R^{2*}$, taken together, may form a ring that is unsubstituted, substituted, or fused to other rings. Amino acceptors include keto carboxylic acids, alkanones (ketones), and alkanals (aldehydes).

"Coenzyme," as used herein, refers to a non-protein compound that operates in combination with an enzyme in catalyzing a reaction. As used herein, "coenzyme" is intended to encompass the vitamin $B_6$ family compounds, PLP, PN, PL, PM, PNP and PMP.

"Pyridoxal-phosphate," "PLP," "pyridoxal-5'-phosphate," "PYP," and "P5P" are used interchangeably to refer to a compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7]. Pyridoxal-5'-phosphate can be produced in vivo by phosphorylation and oxidation of pyridoxol (also known as Vitamin $B_6$). In transamination reactions using transaminase enzymes, the amine group of the amino donor is transferred to the coenzyme to produce a keto by-product, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces an amine and regenerates the coenzyme. In some embodiments, the pyridoxal-5'-phosphate can be replaced by other members of the vitamin $B_6$ family, including pyridoxine (PN), pyridoxal (PL), pyridoxamine (PM), and their phosphorylated counterparts; pyridoxine phosphate (PNP), and pyridoxamine phosphate (PMP).

"Leaving group" is defined as a term that would be understood by one of ordinary skill in the art; that is, a group on a carbon where, upon reaction, a new bond is to be formed and the carbon loses the group upon formation of the new bond. A typical example employing a suitable leaving group is a nucleophilic substitution reaction, e.g., on a $sp^3$ hybridized carbon ($S_N2$ or $S_N1$), e.g. where the leaving group is a halide, such as a bromide, and the reactant might be benzyl bromide. Another typical example of such a reaction is a nucleophilic aromatic substitution reaction (SNAr). Another example is an insertion reaction (for example by a transition metal) into the bond between an aromatic reaction partner bearing a leaving group followed by reductive coupling. "Leaving group" is not limited to such mechanistic restrictions. Examples of suitable leaving groups include halogens (fluorine, chlorine, bromine or iodine), optionally substituted aryl or alkyl sulfonates, phosphonates, azides and —$S(O)_{0-2}R$ where R is, for example, optionally substituted alkyl, optionally substituted aryl, or optionally substituted heteroaryl. Those of skill in the art of organic synthesis will readily identify suitable leaving groups to perform a desired reaction under different reaction conditions. Non-limiting characteristics and examples of leaving groups can be found, for example in Organic Chemistry, 2nd ed., Francis Carey (1992), pages 328-331; Introduction to Organic Chemistry, 2d ed., Andrew Streitwieser and Clayton Heathcock (1981), pages 169-171; and Organic Chemistry, 5th Ed., John McMurry, Brooks/Cole Publishing (2000), pages 398 and 408; all of which are incorporated herein by reference.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," $4^{th}$ Ed., Wiley Interscience (2006), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups.

Representative amine protecting groups include, but are not limited to, formyl, acetyl (Ac), trifluoroacetyl, benzyl (Bn), benzoyl (Bz), carbamate, benzyloxycarbonyl ("CBZ"), p-methoxybenzyl carbonyl (Moz or MeOZ), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), p-methoxybenzyl (PMB), tosyl (Ts) and the like.

As used herein except where noted, "alkyl" is intended to include both branched- and straight-chain saturated aliphatic hydrocarbon groups having the specified number of carbon atoms. For example, "$C_1$-$C_8$" or "$C_{1-8}$," as in "$C_1$-$C_8$ alkyl" or "$C_{1-8}$ alkyl," is defined to include groups having 1, 2, 3, 4, 5, 6, 7 or 8 carbons in a linear or branched arrangement. $C_{1-8}$ alkyl includes all of the hexyl alkyl and pentyl alkyl isomers as well as n-, iso-, sec- and t-butyl, n- and isopropyl, ethyl and methyl. As another example, $C_{1-4}$ alkyl means n-, iso-, sec- and t-butyl, n- and isopropyl, ethyl and methyl. As another example, $C_1$-$C_{10}$ alkyl specifically includes methyl, ethyl, n-propyl, i-propyl, n-butyl, t-butyl, i-butyl, pentyl, hexyl, heptyl, octyl, nonyl, decyl, and so on. If no number is specified, 1-10 carbon atoms are intended for linear or branched alkyl groups. Commonly used abbreviations for alkyl groups are used throughout the specification, e.g. methyl may be represented by conventional abbreviations including "Me" or $CH_3$ or a symbol that is an extended bond without defined terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. The term "cycloalkyl" means a monocyclic saturated aliphatic hydrocarbon group having the specified number of carbon atoms. For example, "cycloalkyl" includes cyclopropyl, methylcyclopropyl, 2,2-dimethyl-cyclobutyl, 2-ethyl-cyclopentyl, cyclohexyl, cyclopentenyl, cyclobutenyl and so on.

"Aryl," unless otherwise indicated, is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring. In an embodiment, aryl is phenyl.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl," as used herein, is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove.

"Protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantio selectivity, the fraction (typically reported as a percentage) of one enantiomer in the sum of both. It is commonly alternatively reported in the art (typically as a percentage) as the enantiomeric excess (e.e.) calculated there from according to the formula [major enantiomer—minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Where a mixture contains more than two diastereomers it is common to report the ratio of diastereomers or "diastereomeric ratio" rather than diastereomeric excess. Enantiomeric excess and diastereomeric excess are types of stereomeric excess.

The term "regioisomers" refers to compounds which have the same molecular formula but differ in the connectivity of the atoms. Accordingly, a regioselective process is one which favors the production of a particular regioisomer over others, e.g., the reaction produces a statistically significant preponderance of a certain regioisomer. A regioselective reaction is a reaction which occurs preferentially at one reactive center rather than another non-identical reactive center.

"Transaminase," "transaminase polypeptide" and "transaminase enzyme," as used interchangeably herein, refer to a polypeptide having an enzymatic capability of transferring an amino group ($NH_2$), a pair of electrons, and a proton from a primary amine of an amino donor to a carbonyl group ($C=O$; i.e., a keto group) of an amino acceptor molecule. Transaminases have been identified from various organisms, such as *Alcaligenes denitrificans, Arthrobacter, Bordetella bronchiseptica, Bordetella parapertussis, Brucella melitensis, Burkholderia malle, Burkholderia pseudomallei, Chromobacterium violaceum, Oceanicola granulosus* HTCC2516, *Oceanobacter* sp. RED65, *Oceanospirillum* sp. MED92, *Pseudomonas putida, Ralstonia solanacearum, Rhizobium meliloti, Rhizobium* sp. (strain NGR234), *Bacillus thuringensis, Vibrio fluvialis* and *Klebsiella pneumoniae* (see, e.g., Shin et al., 2001, Biosci. Biotechnol. Biochem. 65: 1782-1788). Both R-selective and S-selective transaminases are known. The wild-type transaminase from *Arthrobacter* sp. KNK168 is an R-selective, pyridoxal 5'-phosphate (PLP)-dependent enzyme that produces R-amines from some substrates (see, e.g., Iwasaki et al., 2006, Appl. Microbiol. Biotechnol., 69:499-505; U.S. Pat. No. 7,169,592). Non-naturally occurring, engineered transaminase polypeptides generated by human manipulation are available (see, e.g., U.S. application Ser. No. 12/714,397, published as US20100285541; PCT International Appl. serial no. PCT/US2010/025685, published as WO 2010/099501; PCT International Appl. serial no. PCT/US2011/046932, published as WO 2012/024104).

"Naturally-occurring" or "wild-type" refers to the form found in nature. For example, a naturally occurring or wild-type polypeptide or polynucleotide sequence is a sequence that can be isolated from a source in nature and which has not been intentionally modified by human manipulation.

Reaction Conditions

As described further below, and illustrated in the Examples, the present process contemplates ranges of suitable reaction conditions that can be used in the copper-catalyzed carbon-nitrogen coupling and deprotection processes disclosed, including but not limited to ranges of pH, temperature, buffer, solvent system, substrate loading, catalyst loading, ligand loading, atmosphere, and reaction time. Further suitable reaction conditions for carrying out the process steps described herein can be readily optimized by routine experimentation, including by using the methods described in the Examples provided herein; thus, it will be understood that the conditions and/or ranges recited herein are not limitative and only correspond to a mode of the process of the invention.

The term "catalytic amount" is recognized in the art and means a substoichiometric amount relative to a reactant.

"Suitable reaction conditions" refers to those conditions in the reaction solution (e.g., ranges of catalyst and ligand, substrate loading, temperature, pH, buffers, solvents/co-solvents, etc.) under which a copper-catalyst system is capable of coupling an indazole intermediate and a piperidine intermediate as described in detail above.

"Substrate," in the context of the disclosed copper-catalyzed carbon-nitrogen coupling process, refers to the intermediate (pre-coupled) compounds, e.g., the indazole and piperidine compounds disclosed herein.

In certain embodiments of the process, the temperature of the suitable reaction conditions can be chosen to maximize the reaction rate at higher temperatures while maintaining the activity of the catalysis reaction for efficient synthesis. In certain embodiments, the carbon-nitrogen coupling reaction of the present invention is conducted at a temperature between about 90° C. and about 130° C. In one embodiment, the carbon-nitrogen coupling reaction of the present invention is conducted at a temperature equal to or less than about 130° C. In certain embodiments, the carbon-nitrogen coupling reaction of the present invention is conducted at a temperature equal to or less than about 120° C. In certain embodiments, the carbon-nitrogen coupling reaction of the present invention is conducted at a temperature equal to or less than about 110° C. In certain embodiments, the carbon-nitrogen coupling reaction of the present invention is conducted at a temperature equal to or less than about 100° C. In certain embodiments, the carbon-nitrogen coupling reaction of the present invention is conducted at a temperature between about 100° C. to about 110° C. In certain embodiments, the carbon-nitrogen coupling reaction of the present invention is conducted at a temperature about 90° C. In certain embodiments, the carbon-nitrogen coupling reaction of the present invention is conducted at a temperature about 100° C. In certain embodiments, the carbon-nitrogen coupling reaction of the present invention is conducted at a temperature about 110° C.

In certain embodiments, the process steps of the present invention can be carried out at the pH of the solution at the time of initial reactant mixing and may be maintained at a desired pH or within a desired pH range by the addition of an acid or a base during the course of the reaction. In certain embodiments of the process, the pH of the reaction mixture may be allowed to change, or be changed during the course of the reaction. Alternatively, a buffer of buffering system may be used to maintain the reaction at a desired pH. Suitable buffers to maintain desired pH ranges are known in the art and include, for example, phosphate buffer, triethanolamine buffer, and the like. Combinations of buffering and acid or base addition may also be used.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are not generally critical to the success of the reaction and may be accomplished in any conventional fashion. The reactants may be added together at the same time to a solvent, or alternatively, some of the reactants may be added separately, and some together at different time points. In certain embodiments, it is preferable to perform the reactions under an inert atmosphere of a gas such as nitrogen or argon.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be affected by the incremental addition of one of the starting materials to the other. Also, the reaction steps can be combined by the joint addition of the starting materials to the copper catalyst. When complete conversion is not desired or not obtainable, the starting materials can be separated from the product and then recycled back into the reaction zone.

The processes may be conducted in either glass-lined, stainless steel or similar type reaction equipment. The reaction zone may be fitted with one or more internal and/or external heat exchanger(s) in order to control undue temperature fluctuations, or to prevent any possible "runaway" reaction temperatures. Furthermore, one or more of the reactants or the catalyst can be immobilized by attachment to or incorporation into a polymer or other insoluble matrix.

The quantities of reactants used in the process steps of the present invention reaction will generally vary depending on the quantities of product desired, and concomitantly the amount of catalyst and substrates employed. Those having ordinary skill in the art will readily understand how to vary these quantities to tailor them to the desired level of productivity and scale of production. Transformation of substrates to product can be monitored using known methods by detecting substrate and/or product. Suitable methods include gas chromatography, HPLC, and the like.

These and other aspects of the invention will be apparent from the teachings contained herein.

EXAMPLES

Examples provided are intended to assist in a further understanding of the invention. Particular materials employed, species and conditions are intended to be illustrative of the invention and not limiting of the reasonable scope thereof.

Certain starting materials and reagents are either commercially available or known in the chemical scientific or patent literature. Purification procedures include, for example, distillation, crystallization, and normal or reverse phase high performance liquid chromatography.

The abbreviations used herein have the following tabulated meanings (see Table 1). Abbreviations not tabulated below have their meanings as commonly used unless specifically stated otherwise.

TABLE 1

| | |
|---|---|
| MTBE = | Methyl-tert-butyl ether |
| NaOH = | Sodium hydroxide |
| $AlCl_3$ = | Aluminum chloride |
| $H_2SO_4$ = | Sulfuric acid |
| IPA = | Isopropyl alcohol |
| $Na_2CO_3$ = | Sodium carbonate |
| $MgSO_4$ = | Magnesium sulfate |
| $Me_3SOI$ = | Trimethyl sulfoxonium iodide |
| $KOt-Bu_{(s)}$ = | Potassium tert-butoxide |
| DMSO = | Dimethyl sulfoxide |
| THF = | Tetrahydrofuran |
| $Na_2SO_4$ = | Sodium sulfate |
| $ZnBr_2$ = | Zinc bromide |
| $NaHSO_3$ = | Sodium bisulfite |
| PhMe = | Toluene |
| NaCl = | Sodium chloride |
| $iPrNH_2$ = | Isopropylamine |
| MeCN = | Acetonitrile |
| PLP = | Pyridoxal-phosphate |
| $NaBH_4$ = | Sodium borohydride |
| EtOH = | Ethanol |
| $BF_3 \cdot THF$ = | Boron trifluoride tetrahydrofuran complex |
| MeOH = | Methanol |
| $NH_4OH$ = | Ammonium hydroxide |
| LCAP = | Liquid chromatography area percent |
| p-TsOH = | p-Toluenesulfonic acid |
| $(BOC)_2O$ = | Di-tert-butyl dicarbonate |
| DMAc = | Dimethylacetamide |
| DMF = | Dimethylformamide |
| CDI = | 1,1'-Carbonyldiimidazole |
| $t-BuNH_2$ = | tert-butylamine |
| CuBr = | Copper bromide |
| MSA = | Methanesulfonic acid |
| DIPEA = | Diisopropylethylamine |

Example 1

The following Example 1 describes synthesis of the compound 2-{4-[(3S)-Piperidin-3-yl]phenyl}-2H-indazole-7-carboxamide:

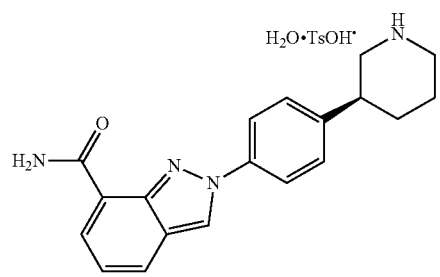

2-{4-[(3S)-Piperidin-3-yl]phenyl}-2H-indazole-7-carboxamide tosylate monohydrate 1

Scheme
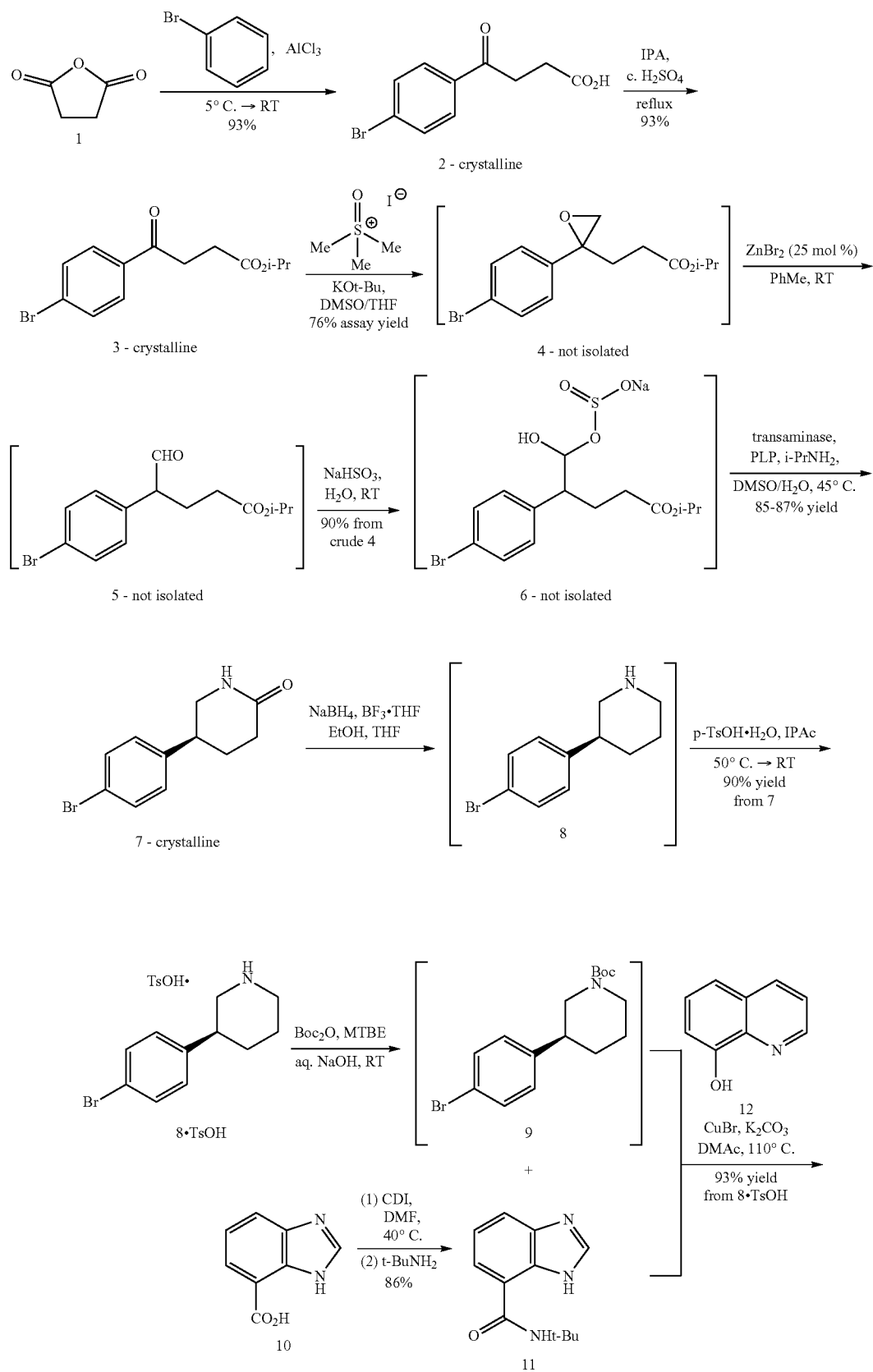

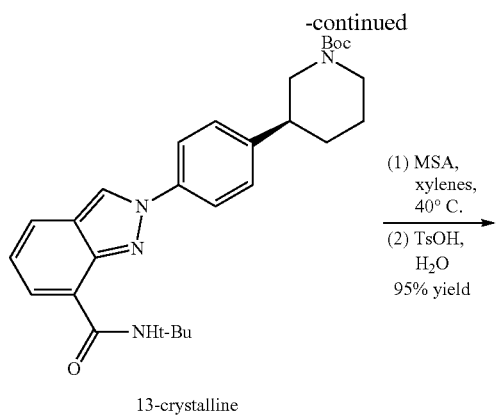

13-crystalline (1) MSA, xylenes, 40° C.
(2) TsOH, H₂O
95% yield

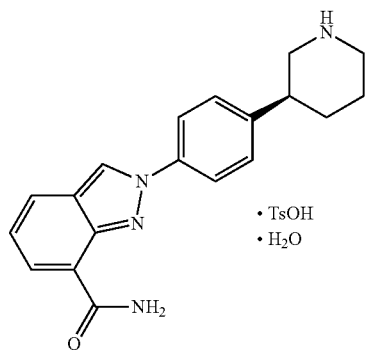

14

1.1 Acylation

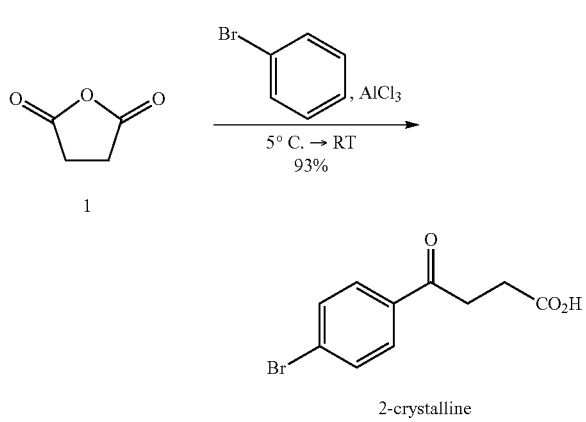

A mixture of succinic anhydride 1 (110 g) and bromobenzene (695 mL) was cooled to below 5° C. then added AlCl₃ (294 g). The slurry was allowed to warm to RT and then aged until the reaction was complete judged by HPLC. The reaction mixture was then transferred slowly into a cold HCl solution resulting in the formation of a white precipitate. The white slurry was filtered through a fritted funnel rinsing with H₂O. To the off-white product was added MTBE and extracted with aq. NaOH. The aqueous layer was cooled in an ice bath. Concentrated HCl was added drop wise to adjust the solution pH to 1, resulting in the formation of a white slurry. The slurry was collected on a fritted funnel, rinsed with H₂O, and dried under vacuum with a N₂ sweep at RT to give the target compound (265 g, 93% corrected yield) as a white powder.

1.2 Esterification

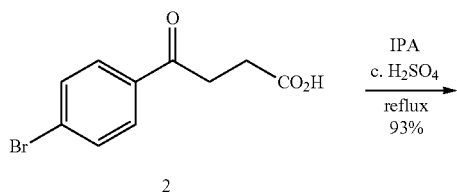

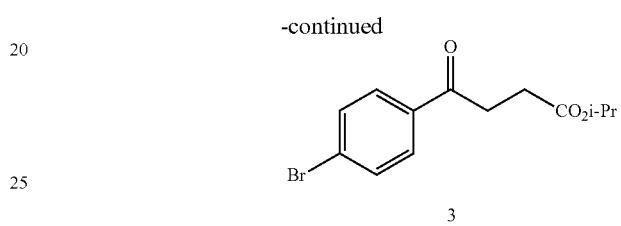

3

A mixture of the acid 2 (205 g), IPA (4 L) and conc. H₂SO₄ (2.13 mL/3.91 g) was heated to a gentle reflux until the reaction was complete judged by HPLC. The solution was then cooled to RT and concentrated to a volume of 350-400 mL. The residue was dissolved in MTBE (1.2 L), washed with aq. Na₂CO₃ followed by water. After dried over MgSO₄, the filtrate was solvent-switched into heptane. The slurry was then filtered, and the cake was washed with cold heptane. After drying under vacuum, the target compound (223.5 g, 93% corrected yield) was obtained as a white powder.

1.3 Epoxidation

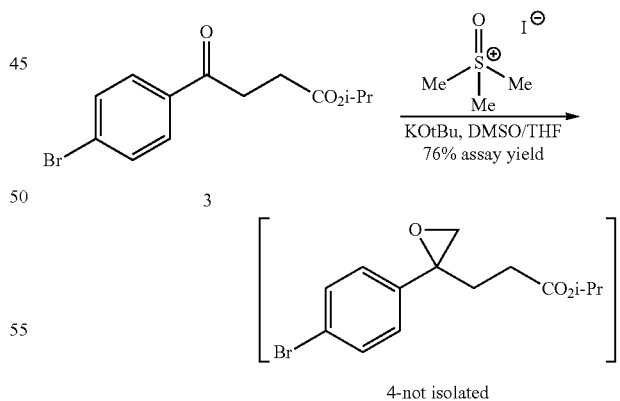

4-not isolated

A mixture of Me₃SOI (230 g) and DMSO (300 mL) was added KOt-Bu (113 g) followed by DMSO (300 mL). The mixture was aged for a further 1.5 hr. In a separate flask, ketone 3 (230 g) was dissolved in a mixture of THF (250 mL) and DMSO (150 mL), and the resulting solution was added drop wise to the ylide solution. The mixture was aged for 2 hr at RT, added hexanes (1 L), and then quenched by the addition of ice-water (600 mL). The layers were cut, and the organic layer was washed with water then with brine. The slightly cloudy yellow organic layer was dried over Na₂SO₄ and filtered through a fritted funnel. Product solution assay was 176.1 g (76% assay yield). This solution was carried forward into the rearrangement step.

1.4 Epoxide Rearrangement and Bisulfite Formation

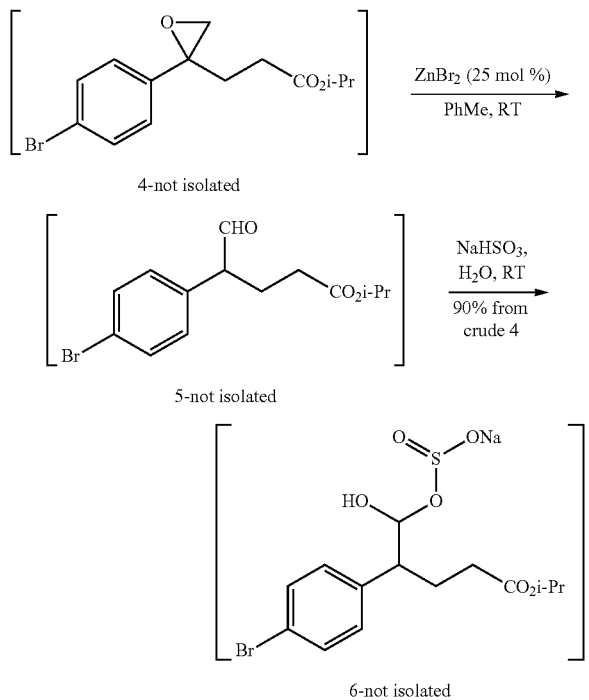

A solution of crude epoxide 4 (assay 59.5 g) in hexanes was solvent switched into PhMe, and added ZnBr₂ (10.7 g). When the rearrangement was complete judged by HPLC, the slurry was filtered through a fritted funnel. The clear filtrate was washed with 10% aq. NaCl and then stirred with a solution of sodium bisulfite (NaHSO₃, 24.7 g) in H₂O (140 mL) vigorously at RT for 3 hr. The cloudy aqueous layer was separated and washed with heptanes. By ¹H-NMR assay, the aqueous solution contained 71.15 g bisulfite adduct 6 (30.4 wt % solution, 90% yield from crude epoxide 4). This solution was used directly in the subsequent transaminase step.

1.5 Transaminase DKR

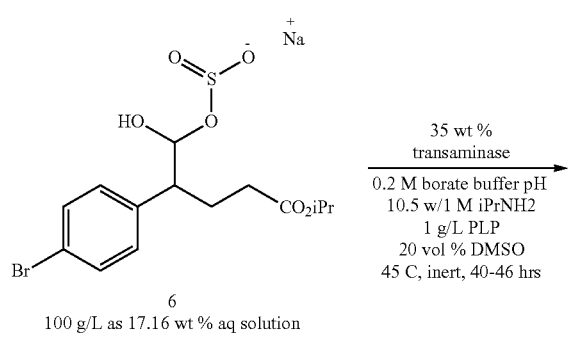

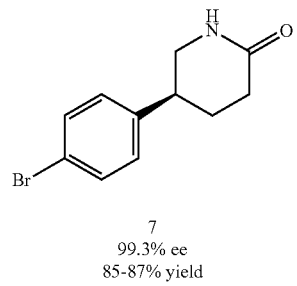

7
99.3% ee
85-87% yield

To a cylindrical Labfors reactor was charged pyridoxal-5-phosphate (1.4 g, 5.66 mmol), 452 ml 0.2 M borate buffer pH 10.5 containing 1M iPrNH₂, 52 g transaminase (SEQ ID NO: 180), and 75 ml DMSO, and the resulting mixture was warmed to 45° C. The pH was controlled at pH 10.5 using 8 M aq iPrNH₂. To this was added dropwise a mixture of 17.16 wt % aq solution of ester bi-sulfite 6 (147.2 g, 353 mmol) and 219 ml DMSO under N₂ atmosphere. When the reaction was complete judged by HPLC, the reaction mixture was cooled and extracted with 1 volume of 3:2 IPA:IPAc. The aq/rag layer was extracted again with 1 volume of 3:7 IPA:IPAc. The organic layer was washed with brine at pH>9. Assay yield in solution was 78 g (87%); 99.3% ee. After dried over MgSO₄, and filtered through a fritted funnel, the crude solution was concentrated under vacuum flushing with IPAc to remove IPA. The resulting slurry was concentrated to a final volume of ~200 mL, cool to below 0° C., and filtered to collect the solid. The cake was washed with ice-cold IPAc and dried at RT under vacuum to give the desired product (84% corrected yield, 99.3 LCAP) as a white powder.

1.6 Reduction of Amide

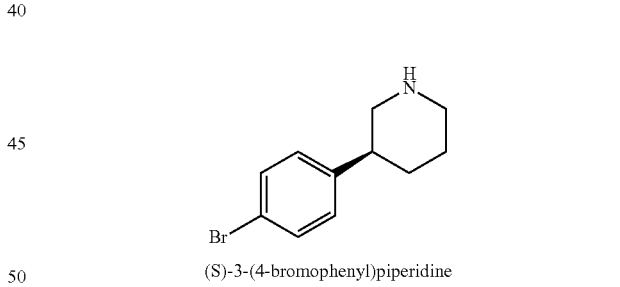

(S)-3-(4-bromophenyl)piperidine

The lactam 7 can be reduced to form the piperidine 8 as described below:

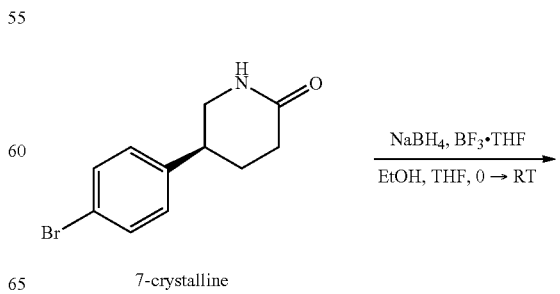

7-crystalline

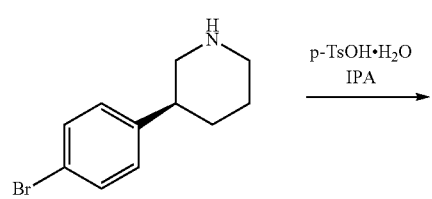

8

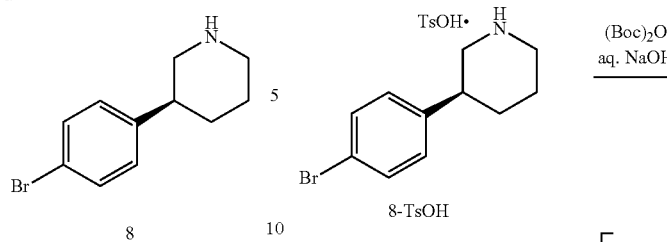

A mixture of lactam 7 (10.25 g at 97.5 wt %) in THF (100 mL) was cooled to <10° C., and added NaBH₄ (4.47 g). EtOH (6.89 mL) was then added slowly over 20 min. The slurry was aged for an additional 1 hr at 2° C. after which BF₃.THF (13.03 mL) was added over 1 hr. The slurry was slowly warmed to RT and aged until complete conversion judged by HPLC. The reaction was then cooled to <5° C. then slowly quenched with MeOH (7.96 mL), added HCl (9.69 mL), then the reaction was heated to 45° C. until decomplexation of product-borane complex was complete, as indicated by LC assay. The reaction was cooled, diluted with IPAc (75 mL) and water (80 mL), and then pH was adjusted with aqueous NH₄OH to pH 8. The organic layer was separated, added 75 mL water, then pH adjusted to 10.5 with 50 wt % NaOH. The layers were separated and the organic layer was washed with brine. After solvent-switched to IPAc, LC Assay yield was 9.1 g; 95.9%.

1.7 Tosylate Salt Formation

The tosylate salt of the piperidine 8 can be formed as described below:

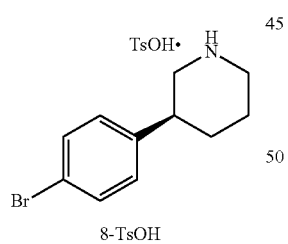

The crude piperidine 8 free base in IPA was heated to ~40° C. TsOH.H₂O solids was added portion-wise. The slurry was warmed to 50° C. and held at that temperature for 2 h, and then slowly cooled to RT and aged overnight. Supernatant concentration was measured to be 2.5 g/ml (free base concentration). The solids were filtered and washed with IPAc (3×15 mL) and dried at RT. Isolated solides: 14.85 g, 96% corrected isolated yield.

1.8 Boc Protection

The piperidine 8 tosylate salt can be protected as described below:

To a stirred slurry of the tosylate salt of piperidine 8 (25.03 g, 60.6 mmol) in MTBE (375 ml) was added NaOH (aq. 1.0 N, 72.7 ml, 72.7 mmol) at RT. To the mixture, (BOC)₂O (13.36 ml, 57.6 mmol) was added slowly over 3 min. The resulting mixture was stirred for 4.5 hr at RT, and then the aqueous layer was separated. The MTBE layer was washed with water (100 ml×2). The organic layer was filtered, and DMAC (100 ml) was added to the filtrate and concentrated under vacuum. Product assay: 21.86 g, quantitative yield.

1.9 Tert-Butylamide Formation

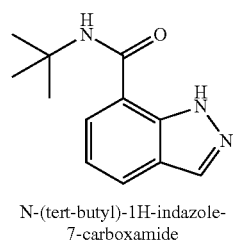 [SMILES: CC(C)(C)NC(=O)c1cccc2cn[nH]c12]

N-(tert-butyl)-1H-indazole-
7-carboxamide

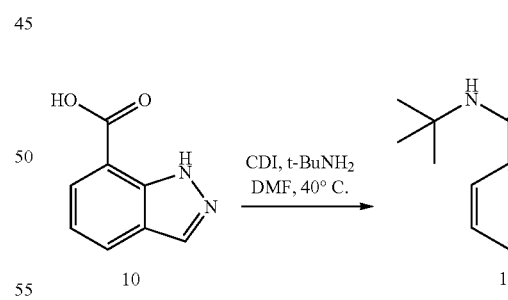

Indazole-7-carboxylic acid 10 (50.3 g, 295 mmol) was dissolved in DMF, and added CDI (59.1 g, 354 mmol) at RT. After 1.5 hr, tert-butylamine (62.5 ml, 589 mmol) was added to the reaction mixture. The resulting reaction mixture was warmed to 40° C. until complete conversion, then cooled to RT. Water (600 ml) was added dropwise causing the mixture to form a thick slurry. Solid was collected by filtration and washed with 10% DMF in water (250 ml) followed by water. The solid was dried under vacuum. Beige solid: 55.31 g, 86% isolated yield.

1.10 Carbon-Nitrogen Coupling

1.11 Double Deprotection

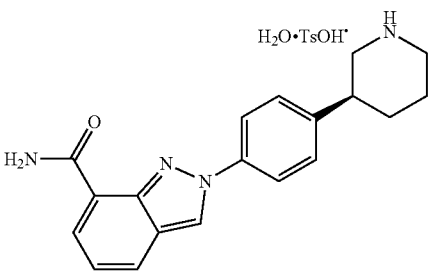

2-{4-[(3S)-Piperidin-3-yl]phenyl}-2H-indazole-7-carboxamide tosylate monohydrate 1

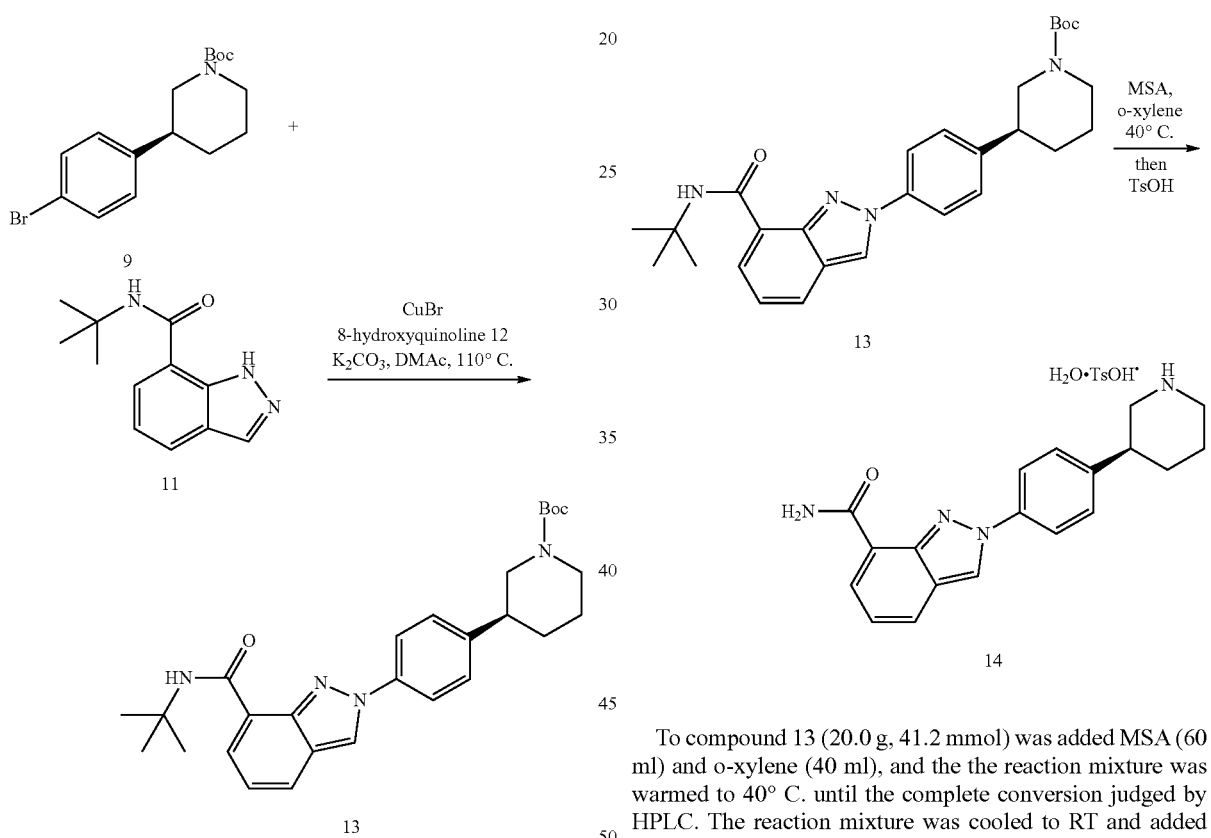

A mixture of the protected piperidine 9 (113 g, 18.23 wt %, 60.6 mmol) in DMAc (160 mL), compound 11 (13.82 g, 63.6 mmol), and K$_2$CO$_3$ (25.6 g, 182 mmol) was degassed by bubbling nitrogen. To the mixture was added CuBr (0.444 g, 3.03 mmol) and 8-hydroxyquinoline 12 (0.889 g, 6.06 mmol), and the resulting mixture was warmed to 110° C. until complete conversion. The reaction mixture was then cooled, filtered through a pad of Celite, and rinsed with DMAc (100 ml). The filtrate was warmed to 35° C. and added citric acid aqueous solution (10%) dropwise to form a light green slurry. After cooled to room temperature, the slurry was filtered, and the cake was washed with DMAc/Water (2/1, 150 ml) followed by copious amount of water. The solid was dried under vacuum with nitrogen. Net weight: 27.24 g. LC assay: 26.77 g, 98.3 wt %. Assay yield: 93.6%.

To compound 13 (20.0 g, 41.2 mmol) was added MSA (60 ml) and o-xylene (40 ml), and the the reaction mixture was warmed to 40° C. until the complete conversion judged by HPLC. The reaction mixture was cooled to RT and added water (140 ml) slowly maintaining the temperature<25° C. When the water addition was completed, the organic layer was removed, and the aq. layer was washed with toluene. The aqueous layer was filtered through a glass funnel, and the filtrate was added an aqueous solution of TsOH (11.77 g in 23.5 ml) slowly at RT causing a thick slurry to form. Solid was collected by filtration, washed with water, and dried under vacuum. The titled compound was obtained as a white powder. Net weight: 20.6 g. LC assay: 20.0 g, 97.3 wt %. Assay yield: 95.2%.

Example 2

The following Example 2 describes synthesis of the trifluoromethylacetate salt of compound 2-{4-[(3S)-Piperidin-3-yl]phenyl}-2H-indazole-7-carboxamide:

2.1 Cumylamide Formation

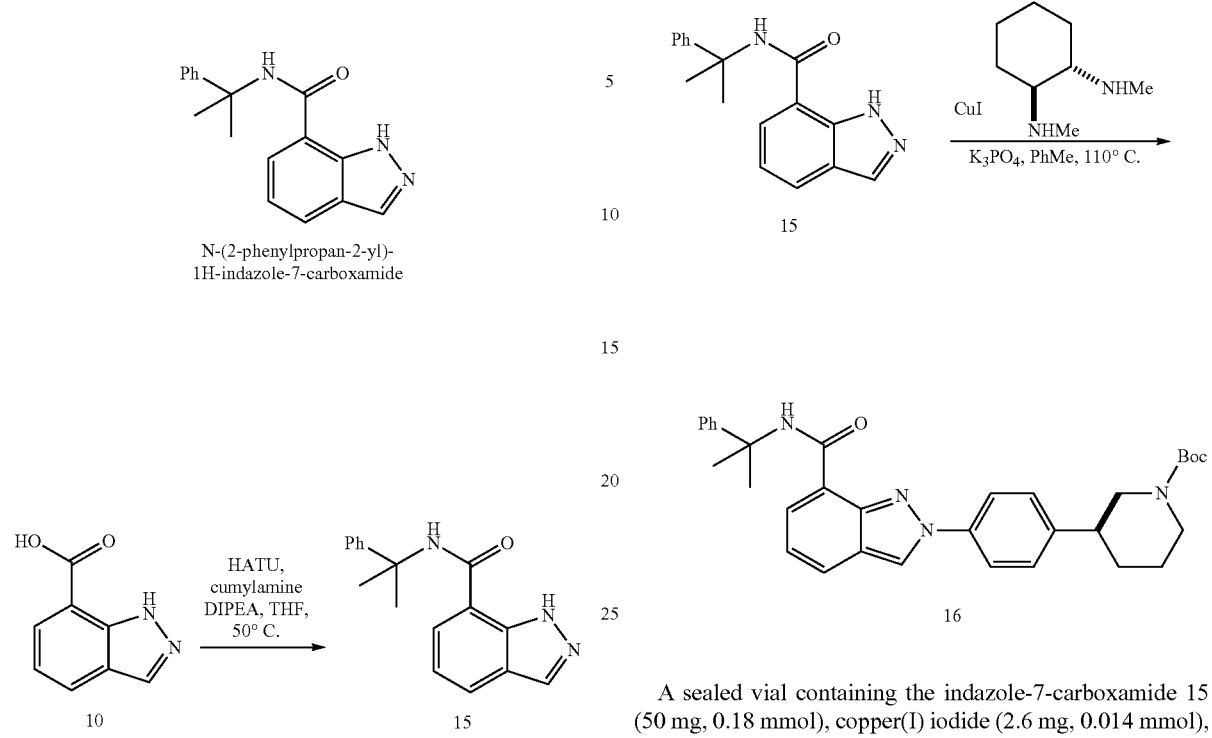

To the indazole-7-carboxylic acid 10 (400 mg, 2.47 mmol) in tetrahydrofuran (9.9 mL), was sequentially added HATU (1.13 g, 2.96 mmol), DIPEA (2.15 mL, 12.3 mmol), and cumylamine (500 mg, 3.70 mmol) at 50° C. The reaction was stirred overnight before being concentrated and loaded directly onto a silica column, eluting with 10-30% EtOAc/hexane. The product was collected and concentrated to afford the desired product as a colorless solid (557 mg, 81% yield).

2.2 Carbon-Nitrogen Coupling

A sealed vial containing the indazole-7-carboxamide 15 (50 mg, 0.18 mmol), copper(I) iodide (2.6 mg, 0.014 mmol), potassium phosphate tribasic (80 mg, 0.38 mmol), and aryl bromide 9 (73.1 mg, 0.215 mmol) was evacuated and backfilled with argon (×3). Trans-N,N'-dimethylcyclohexane-1,2-diamine (11.3 μL, 0.072 mmol), and toluene (179 μl) were then added successively and the sealed vial was heated at 110° C. overnight. The vial was then cooled and toluene (0.30 mL) was added to the slurry. Crude LC/MS indicated>20:1 selectivity for the desired indazole isomer. The crude product was purified by loading directly onto a Biotage Snap 10G silica column, eluting with 5-50% EtOAc/hexane. The product was collected and concentrated to afford the desired product as a colorless solid (78 mg, 81% yield).

2.3 Double Deprotection

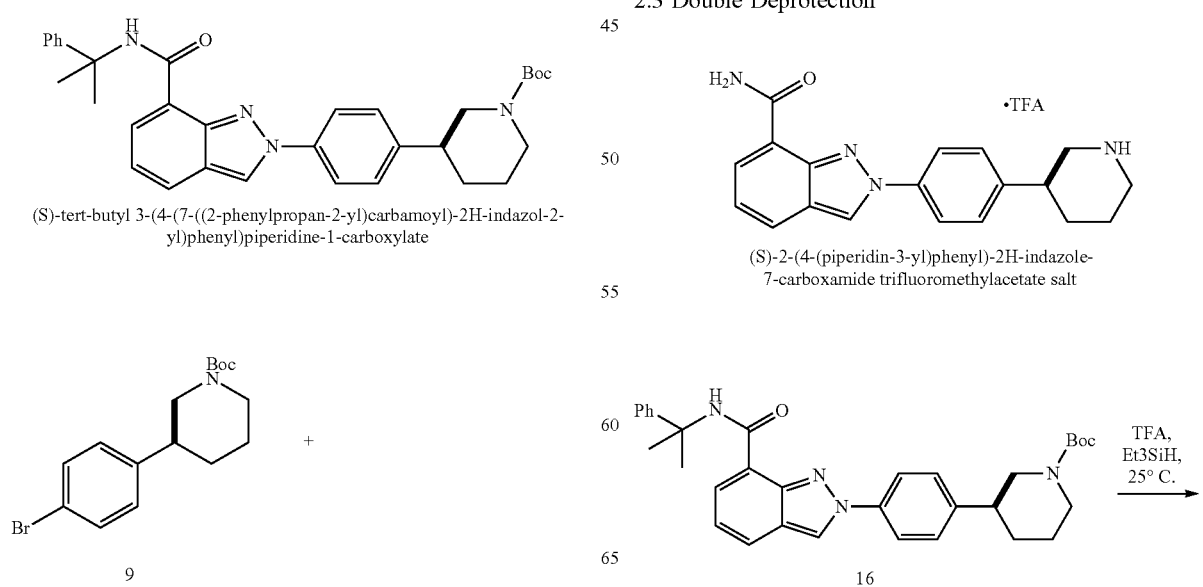

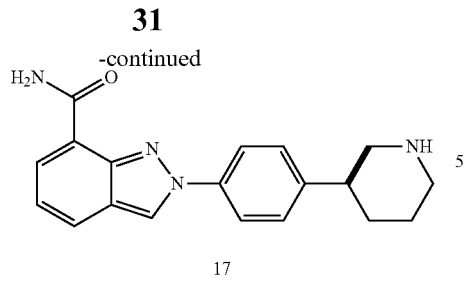

17

To the piperidine-1-carboxylate 16 (45 mg, 0.084 mmol), was added triethylsilane (267 μL, 1.67 mmol) and TFA (0.965 mL, 12.5 mmol) at 25° C. The reaction was stirred for 4 hours and the reaction was concentrated in vacuo, and purified by mass triggered reverse phase HPLC (acetonitrile: water, with 0.1% TFA modifier). Lyphilization gave the desired product as the TFA salt and as a white solid (31 mg, 85% yield). HRMS (ESI) calc'd for $C_{19}H_{21}N_4O$ $[M+H]^+$: 321.1710, found 321.1710.

Example 3

Following the conditions used in sections 2.1 and 2.2 of Example 2, this Example 3 shows regioselective N2 arylation of compound 9 using various amide protecting groups. The indazole-7-carboxylic acid 10 was reacted with various amines to generate a protected amide. The amide protecting groups are indicated by the R group in Table 2. The amide coupling yield is provided in Table 2. The Cu-mediated carbon-nitrogen coupling of this indazole to compound 9 was then tested to determine if regioselective N2 arylation was possible. The arylation yield is also provided in Table 2. The data shows that various amide protecting groups on the indazole intermediate are suitable to generate efficient regioselective N2 arylation of compound 9.

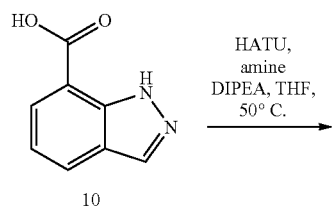

10

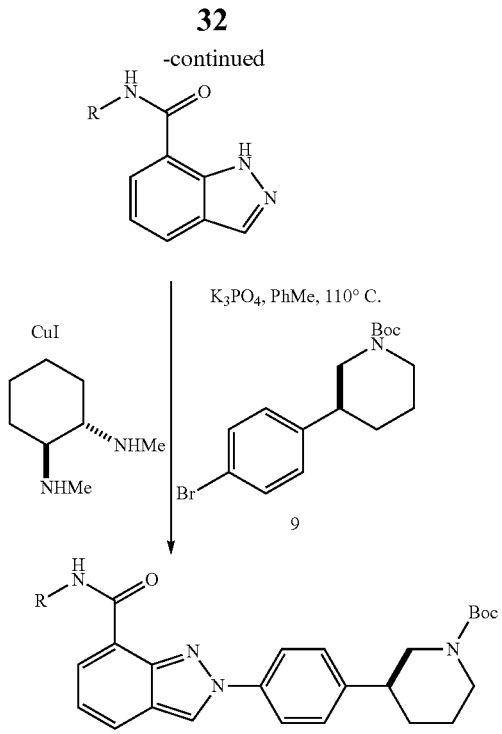

TABLE 2

| R | Amide coupling yield | Cu-Mediated Arylation yield |
|---|---|---|
| ![CPh3] trityl (CPh3) | 52% | 96% |
| ![CH2Ph] benzyl | 80% | 88% |
| ![2,4-dimethoxybenzyl] | 88% | 94% |
| ![CH(CH3)Ph] | 89% | 97% |

What is claimed is:

1. A compound of formula IV:

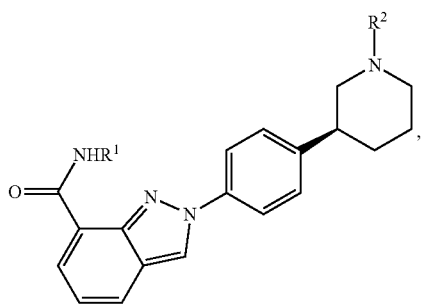

wherein:

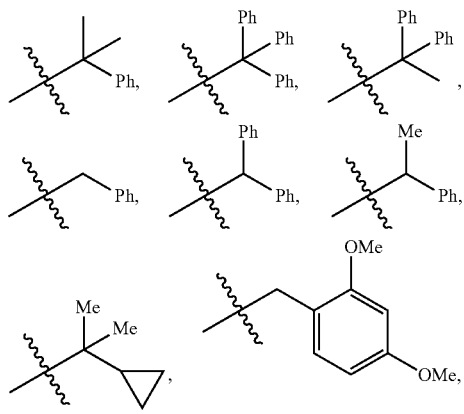

R¹ is C$_{4-8}$ alkyl, C$_{3-10}$ cycloalkyl, C$_{4-10}$ heterocyclyl, aryl, or heteroaryl; and R² is an amine protecting group.

2. The compound of claim 1, wherein R¹ is t-butyl, cumyl, or trityl.

3. The compound of claim 1, wherein the amine protecting group is selected from the group consisting of formyl, acetyl, trifluoroacetyl, benzyl, benzoyl, carbamate, benzyloxycarbonyl, p-methoxybenzyl carbonyl, tert-butoxycarbonyl, trimethylsilyl, 2-trimethylsilyl-ethanesulfonyl, trityl, substituted trityl groups, allyloxycarbonyl, 9-fluorenylmethyloxycarbonyl, nitro-veratryloxycarbonyl, p-methoxybenzyl, and tosyl.

4. The compound of claim 1, wherein the amine protecting group is tert-butoxycarbonyl.

5. The compound of claim 2, wherein the amine protecting group is selected from the group consisting of formyl, acetyl, trifluoroacetyl, benzyl, benzoyl, carbamate, benzyloxycarbonyl, p-methoxybenzyl carbonyl, tert-butoxycarbonyl, trimethylsilyl, 2-trimethylsilyl-ethanesulfonyl, trityl, substituted trityl groups, allyloxycarbonyl, 9-fluorenylmethyloxycarbonyl, nitro-veratryloxycarbonyl, p-methoxybenzyl, and tosyl.

6. The compound of claim 2, wherein the amine protecting group is tert-butoxycarbonyl.

7. The compound of claim 1, wherein R¹ is t-butyl and R² is tert-butoxycarbonyl, which is (S)-tert-butyl 3-(4-(7-(tert-butylcarbamoyl)-2H-indazol-2-yl)phenyl)piperidine-1-carboxylate:

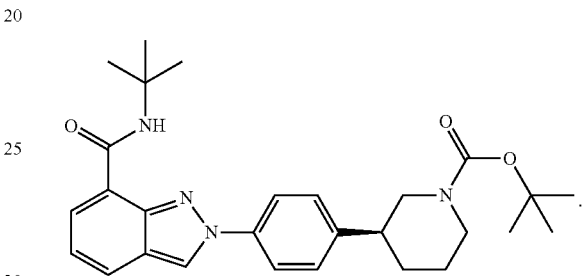

8. The compound of claim 1, wherein R¹ is cumyl and R² is tert-butoxycarbonyl, which is (S)-tert-butyl 3-(4-(7-((2-phenylpropan-2-yl)carbmoyl)-2H-indazol-2-yl)phenyl)piperidine-1-carboxylate:

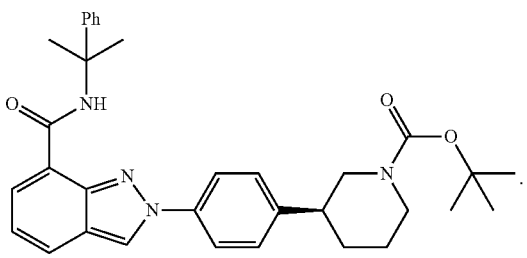 [SMILES: CC(C)(C)OC(=O)N1CCC[C@@H](c2ccc(-n3cc4cccc(C(=O)NC(C)(C)c5ccccc5)c4n3)cc2)C1]

* * * * *

SEQUENCE LISTING

<160> NUMBER OF SEQ ID NOS: 2

<210> SEQ ID NO 1
<211> LENGTH: 330
<212> TYPE: PRT
<213> ORGANISM: Artificial Sequence
<220> FEATURE:
<223> OTHER INFORMATION: Engineered variant of Arthrobacter transaminase

```
<400> SEQUENCE: 1

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ile Val Ser Ile Thr
            115                 120                 125

Arg Gly Tyr Ser Ser Thr Pro Trp Glu Arg Asp Ile Thr Lys His Arg
130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 2
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 2

Met Ser Phe Ser His Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
```

```
                    20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Phe Tyr Thr Ser Asp
 50                  55                  60

Ala Thr Tyr Thr Val Phe His Val Trp Asn Gly Asn Ala Phe Arg Leu
 65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
               100                 105                 110

Val Ala Lys Thr Glu Leu Arg Glu Ala Ile Val Ile Val Ser Ile Thr
               115                 120                 125

Arg Gly Tyr Ser Ser Thr Pro Trp Glu Arg Asp Ile Thr Lys His Arg
               130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
               165                 170                 175

Arg Thr Pro Arg Ser Ser Ile Asp Pro Gln Val Lys Asn Phe Gln Trp
               180                 185                 190

Gly Asp Leu Ile Arg Ala Ile Gln Glu Thr His Asp Arg Gly Phe Glu
               195                 200                 205

Leu Pro Leu Leu Leu Asp Phe Asp Asn Leu Leu Ala Glu Gly Pro Gly
               210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
               245                 250                 255

Ser Leu Gly His Glu Ala Ile Leu Ala Asp Ile Thr Pro Ala Glu Leu
               260                 265                 270

Tyr Asp Ala Asp Glu Val Leu Gly Cys Ser Thr Gly Gly Gly Val Trp
               275                 280                 285

Pro Phe Val Ser Val Asp Gly Asn Ser Ile Ser Asp Gly Val Pro Gly
               290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
               325                 330
```